United States Patent
Beck, III et al.

(10) Patent No.: US 6,371,698 B1
(45) Date of Patent: Apr. 16, 2002

(54) POST STRESSED PIER

(75) Inventors: August H. Beck, III; Philip G. King, both of San Antonio, TX (US)

(73) Assignee: A. H. Beck Foundation Company, Inc., San Antonio, TX (US)

( * ) Notice: Subject to any disclaimer, the term of this patent is extended or adjusted under 35 U.S.C. 154(b) by 0 days.

(21) Appl. No.: 09/435,807

(22) Filed: Nov. 8, 1999

(51) Int. Cl.$^7$ .......................... G01N 3/00; E02D 15/04; E02D 5/36; E02D 5/58
(52) U.S. Cl. .................. 405/236; 405/248; 405/256; 73/785; 73/786
(58) Field of Search ................................ 405/231–233, 405/236, 239, 248, 249, 256; 73/784–786, 84

(56) References Cited

U.S. PATENT DOCUMENTS

| | | | |
|---|---|---|---|
| 3,503,254 A | 3/1970 | Menard | 73/784 |
| 3,633,408 A | 1/1972 | Johnston, Jr. | 73/784 |
| 3,772,911 A | 11/1973 | Ruppeneit et al. | 73/784 |
| 3,793,844 A | * 2/1974 | Chelminski | 405/248 X |
| 4,315,429 A | 2/1982 | Morozov et al. | 73/84 |
| 4,458,525 A | 7/1984 | Lutenegger et al. | 73/84 |
| 4,483,197 A | 11/1984 | Kellner | 73/784 |
| 4,598,591 A | * 7/1986 | Baud | 73/784 |
| 4,614,110 A | 9/1986 | Osterberg | 73/84 |
| 4,662,213 A | 5/1987 | Handy et al. | 73/37 |
| 4,663,977 A | 5/1987 | Vander Heyden | 73/861.27 |
| 4,722,407 A | 2/1988 | Gindy et al. | 177/50 |
| 5,185,595 A | * 2/1993 | Friesen | 73/784 X |
| 5,259,240 A | 11/1993 | Raines et al. | 73/84 |
| 5,319,959 A | 6/1994 | Cooper et al. | 73/84 |
| 5,377,548 A | 1/1995 | Ballivy | 73/768 |
| 5,576,494 A | 11/1996 | Osterberg | 73/784 |
| 5,739,435 A | * 4/1998 | Sacks | 73/784 |
| 5,823,718 A | * 10/1998 | DuPlessis | 405/233 X |

FOREIGN PATENT DOCUMENTS

| | | |
|---|---|---|
| DE | 150089 | 8/1981 |
| GB | 1413160 | 11/1975 |
| RU | 585397 | 12/1977 |

OTHER PUBLICATIONS

Article: Foundation with Grouted Base Piles, United States Embassy (Egypt) Author: Author not listed Date: No date listed.

Report entitled: "Drilled Shafts: Effects of Construction on Performance and Design Criteria" Author: Michael W. O'Neill and Khaled M. Hassan Date: No date listed.

Abstract from Report: "O–Cell Testing Case Histories Demonstrate The Importance of Bored Pile (Drilled Shaft) Construction Technique" Author: Author not listed Date: 1988.

Article: Foundation with Grouted Base Piles Misr. International Tower (Egypt) Author: Author not listed Date: No date listed.

Article: Foundation: Foundation with Grouted Base Piles, Steel Plant Jubail (Saudi–Arabia) Author: Author not listed Date: No date listed.

Article: Foundation with Grouted Base Piles, Jeddah–Mecca–Expressway Date: No date listed.

* cited by examiner

Primary Examiner—Thomas B. Will
Assistant Examiner—Tara L. Mayo
(74) Attorney, Agent, or Firm—Akin, Gump, Strauss, Hauer & Feld, L.L.P.

(57) ABSTRACT

A structural pier assembly includes a cementitious pier and pressurized grout contained beneath the pier in the shaft so as to exert an upward force on the pier. An enclosure, such as a bladder or bellows, is filled with grout from a reservoir via a conduit which preferably extends axially along the length of the pier and is left in place after the grout hardens. A pressure gauge measures the pressure of the grout within the enclosure, permitting the direct measurement of end bearing and side bearing capacities of the resulting pier assembly. The load bearing capacity of the pier is enhanced by the pressurized grout, and is preferably at least twice the end bearing capacity of an unpressurized pier.

29 Claims, 4 Drawing Sheets

POST STRESSED PIER

FIELD OF THE INVENTION

The invention relates generally to techniques for increasing the load bearing capacity of structural foundation piers, and more particularly to the use of structures or devices placed beneath or within piers to enhance load bearing.

BACKGROUND OF THE INVENTION

Drilled shafts, or piers, are often used in the deep foundation industry because they provide an economical alternative to other types of deep foundations. Drilled piers are typically formed by excavating a cylindrical borehole in the ground and then placing reinforcing steel and fluid concrete in the borehole. The excavation may be assisted by the use of drilling fluids, casements or the like. When the concrete hardens, a structural pier suitable for load bearing results. These piers may be several feet in diameter and 50 feet or more deep. They are typically designed to support axial and tensile compressive loads.

A finished structural pier has an axial load bearing capacity which is conventionally characterized by components of end bearing ($q_b$) and side bearing, which is a function of skin friction ($f_s$). Loads applied at the top end of the pier are transmitted to the sidewalls of the pier and to the bottom of the pier at the distal end of the shaft. The end bearing capacity is a measure of the maximum load that can be supported there, and it will depend on numerous factors including the diameter of the pier and the composition of the geomaterial (soil, rock, etc.) at the bottom of the shaft. The side bearing capacity is a measure of the amount of load capable of being borne by the skin friction developed between the side of the pier and the geomaterial. It depends on numerous factors, including the composition of the pier and the geomaterial forming the side of the pier, which may vary with length (depth). The sum of the end bearing and side bearing capacities generally represents the total load that can be supported by the pier without sinking or slippage, which could cause destructive movements for a finished building or bridge atop the pier.

Although it is desirable to know the maximum end bearing and side bearing for a particular pier, it is difficult to make such measurements with a high degree of confidence. Foundation engineering principles account for these difficulties by assigning end bearing and load bearing capacities to a pier based on its diameter and depth, the geomaterial at the end of the pier and along its side, and other factors. A safety factor is then typically applied to the calculated end bearing and side bearing capacities. These safety factors are chosen to account for the large number of unknown factors that may adversely affect side bearing and end bearing, including geomaterial stress states and properties, borehole roughness generated by the drilling process, geomaterial degradation at the borehole-shaft interface during drilling, length of time the borehole remains open prior to the placement of concrete, residual effects of drilling fluids, borehole wall stresses produced by concrete placement, and other construction-related details. For example, it is common to apply a safety factor of 2 to the side bearing so as to reduce by half the amount calculated to be borne by skin friction. Likewise, a safety factor of 3 is often applied to the calculated end bearing capacity, reflecting the foregoing design uncertainties and others.

The use of safety factors, although judiciously accounting for many of the uncertainties in drilled shaft pier construction, often results in piers being assigned safe load capacities that are too conservative. To compensate, builders construct larger, deeper, and/or more piers than are necessary to safely support a structural load, unnecessarily increasing the time, effort and expense of constructing a suitable foundation.

As a partial solution, it has been known to directly measure the end bearing capacity and skin friction of a drilled-shaft pier. Osterberg (U.S. Pat. No. 4,614,110) discloses a parallel-plate bellows placed in the bottom of the shaft before the concrete pier is poured. The bellows are pressured up with fluid communicated through a pipe coaxial with the pier. Skin friction is determined by measuring the vertical displacement of the pier (corresponding to the movement of the upper bellows plate) as a function of pressure in the bellows. Likewise, end bearing is determined by measuring pressure against the downward movement of the lower bellows plate, as indicated by a rod affixed thereto and extending above the surface through the fluid pipe. Upon completion of the load test, the bellows are depressurized. The bellows may then be abandoned or filled with cement grout, and in the latter case becomes in essence an extension of the lower end of the pier.

The method of Osterberg most often serves only the purpose of load testing. In practice, most often a drilled shaft employing the "Osterberg cell" is abandoned after testing in favor of nearby shafts that do not contain a non-functioning testing cell at their base.

Other methods have been developed for enhancing the load bearing capacity of drilled shaft piers by permanently pressuring up the base, but they lack the testing capabilities of the Osterberg cell. For example, it is known to inject pressurized cement grout under the base of concrete piers to enhance load bearing. In post-grouting, the pressurized grout increases end bearing, but neither the resultant increase nor the absolute end bearing capacity can be determined from the pressure or volume of the grout. In some soils, skin friction may also be increased by allowing the pressurized grout to flow up around the sides of the shaft, but this side bearing capacity, too, is not determinable with this technique.

SUMMARY OF THE INVENTION

It is therefore desirable to enhance the load bearing capacity of a drilled shaft foundation pier in a manner that permits direct measurement of the resultant end bearing and side bearing capacities of the pier.

Accordingly, an object of the present invention is to provide a simple and convenient technique for directly measuring the end bearing and side bearing capacities of a foundation pier.

Another object of the present invention is to allow a reduction in the safety factors in determining the load bearing capacity of a pier.

Another object of the present invention is to increase the end bearing and side bearing capacities of a foundation pier in a known amount.

Another object of the present invention is to use the same device to aid in measuring the load bearing capacity of a pier and increase its load bearing capacity.

In satisfaction of these and other objects, the invention preferably includes a bladder, cell, or other supporting enclosure placed at the base or within the length of a pier for receiving pressurized grout. The enclosure is filled with pressurized grout to stress the base of the pier. The known pressure of the grout can be used to calculate end bearing and side bearing capacities of the pier. Upon hardening under pressure, the supporting enclosure permanently contributes to increased end bearing and side bearing in a known amount. In the resulting pier assembly, the supporting enclosure in essence becomes an extension forming the lower end of the pier. The post-base-stressed pier assembly has end bearing and side bearing capacities that are enhanced, and are determinable by direct measurement, thus reducing the safety factor used in the pier load bearing capacity calculation.

In one embodiment, the supporting enclosure is a bladder made of a strong material such as thick rubber. The bladder is filled with pressurized grout via a conduit extending axially down the concrete pier to be post-base-stressed. The grout hardens under pressure, and the actual end bearing capacity is calculated from the pressure and the area of the bottom of the shaft. Pressurization of the bladder pushes upward on the concrete pier portion, resulting in additional opposing skin friction in a known amount. Subsequent downward load is opposed by the end bearing, the original skin friction, and the additional skin friction created by the pressurization of the bladder. This additional skin friction is closely related to the end bearing capacity. Accordingly the post-base-stressed pier advantageously has at least twice the known overall load bearing capacity of an unstressed pier.

In another embodiment, the supporting structure comprises hard plates forming opposite ends of bellows. The regular geometry of such plates ensures more uniform application of pressure from the grout against the bottom of the shaft and the lower end of the concrete pier portion.

In yet another embodiment, the post-base-stressed pier assembly need not be formed with an enclosure, but may simply rely on the natural boundaries provided by the shaft bottom and sides and the lower end of the concrete pier portion to receive and contain the pressurized grout.

In yet another embodiment, the supporting assembly is placed within the length of the concrete pier to be post-base-stressed. In this embodiment, a distal pier portion forming a portion of the length of the pier may be formed first, and the supporting assembly placed thereon before the remainder of the length of the pier is formed. The supporting assembly may be either the bladder or bellows structure described above, or post-stressing may occur by injection of grout into an enclosure defined by the side of the shaft and the previously-formed pier portion in the distal end of the shaft.

BRIEF DESCRIPTION OF THE DRAWINGS

The present invention is more easily understood with reference to the drawings, in which.

DETAILED DESCRIPTION OF THE PREFERRED EMBODIMENT

Figure 1:
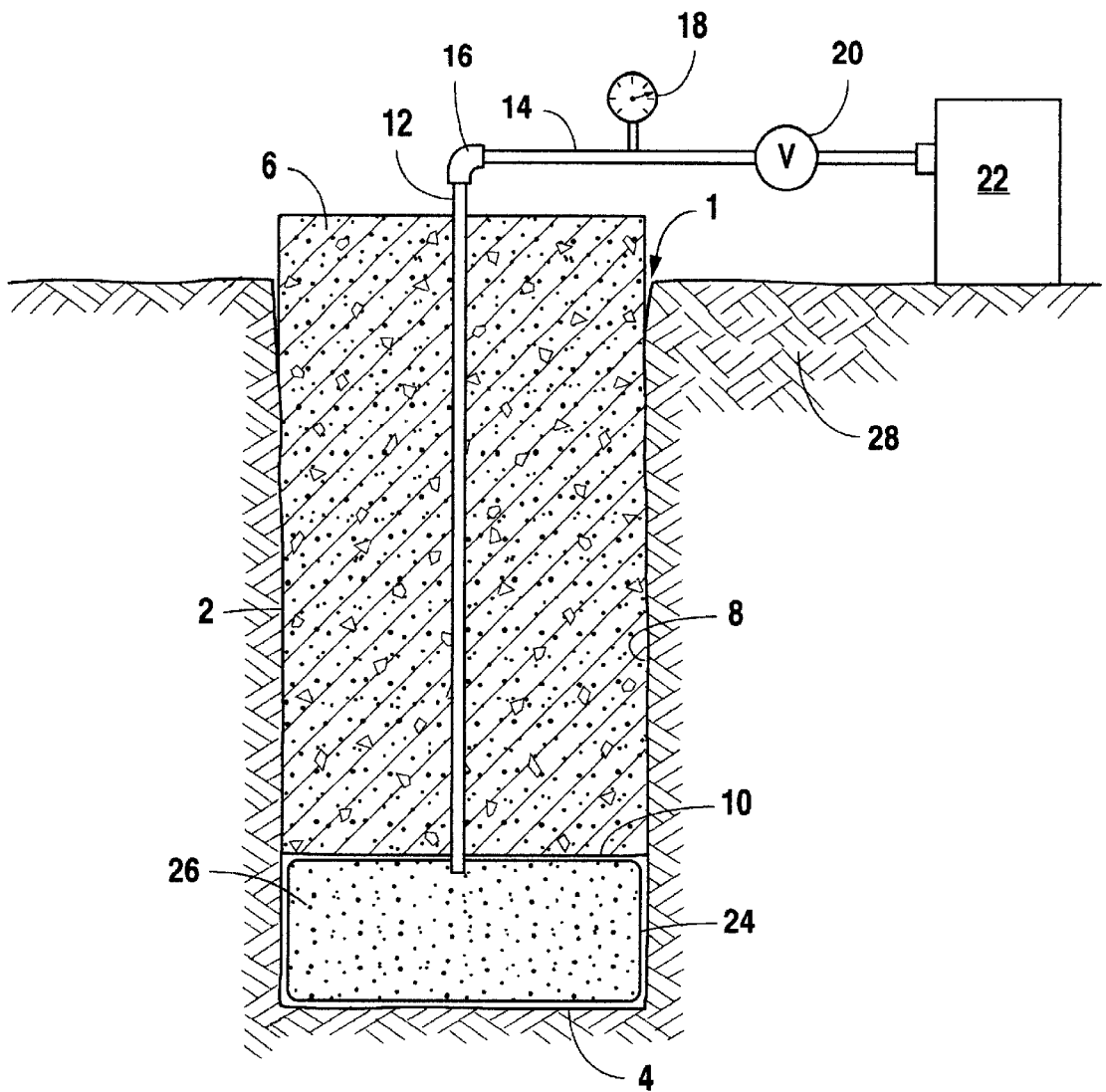
FIG. 1 is a cross-sectional view of the post-base-stressed pier assembly according to the present invention and apparatus for injecting pressurized grout into a supporting bladder thereof.

Referring in more detail to the drawings, there is shown in FIG. 1 apparatus for post-base stressing a concrete pier 6.

Any suitable technique for producing a shaft 1 having a shaft wall 2 and a shaft floor 4 may be employed to commence construction of the pier in earthen material 28. Pier 6 is preferably made of cementitious material such as concrete, and may be formed by conventional techniques, which include the use of steel reinforcing bars or cages to increase the strength of the pile under the influence of torsional forces or tensile loading. Shaft wall 2 exerts skin friction against pier wall 8 commensurate with the weight of the pier and any load placed on it.

Enclosure 24 is placed in the lower end of the shaft 1 before the pier 6 is poured. Enclosure 24 may be any structure capable of containing pressurized grout, and is preferably a thick rubber bladder or cell. After placement of enclosure 24, pier 6, which is preferably cylindrical, is formed in the usual manner. Enclosure 24 is adapted to receive pressurized grout 26 via conduit 12, which is preferably a pipe extending coaxially along the length of pier 6. Conduit 12 may be coupled to enclosure 24 in a variety of ways known to those skilled in the art. Further, it will be apparent to those skilled in the art that pressurized fluid grout may be transmitted to enclosure 6 in a variety of ways, for example, by a conduit extending down the side of the shaft.

Conduit 26 is in fluid communication with reservoir 22 containing fluid grout. In simple fashion, upon opening of valve 20, grout may be pumped from reservoir 22 through a lateral 14, which is joined by elbow 16 to conduit 12. The pressure of grout 26 within enclosure 24 is measured at the surface by a pressure gauge 18. Fluid grout is pumped into enclosure 6 until it fills the cavity bounded by shaft wall 2, shaft floor 4 and lower end 10 of pier 6, whereupon further pumping requires significantly greater pressures due to the weight of pier 6, the skin friction between shaft wall 2 and pier wall 8, and the relative incompressibility of the fluid grout.

Injection of grout under pressure creates an upward force exerted by enclosure 24 against pier 6 at its lower end 10. Injection continues until the pressure indicated by gauge 18 reaches a predetermined threshold or until some other criterion is reached. The maximum load bearing will ordinarily be obtained if pressurization continues until the onset of gross upward movement of pier 6 in the shaft, indicating incipient ejectment of the pier from the shaft. At the desired point, valve 20 is closed and the quiescent pressure within enclosure is obtained by gauge 18.

Direct measurement of the end bearing capacity of the resulting post-base-stressed pier assembly is thereby obtained from the quiescent pressure and the area of shaft floor 4. In a similar manner, the side bearing capacity is directly measured from the quiescent pressure and the area of lower end 10 of the pier. Advantageously, the skin friction exerts a downward force on the post-base-stressed pier to resist the tendency of the pier to be ejected out of the borehole. A load placed on the pier must overcome this skin friction before returning the pier to its initial state, wherein the skin friction exerts an upward force in reaction to the weight of the pier itself. The pier 6 enjoys the benefit of the same skin friction, whether exerted upward or downward against the pier. The post-base-stressing of the pier therefore results in an increase in side bearing capacity in an amount corresponding to the pressurization of the bladder. In addition, because direct measurements of end bearing and side bearing are made, reduced safety factors can be employed. Once the necessary pressure measurements are made, pressurized grout 26 is allowed to harden so that enclosure 24 forms a permanent pressurizing extension of pier 6.

Figure 2:
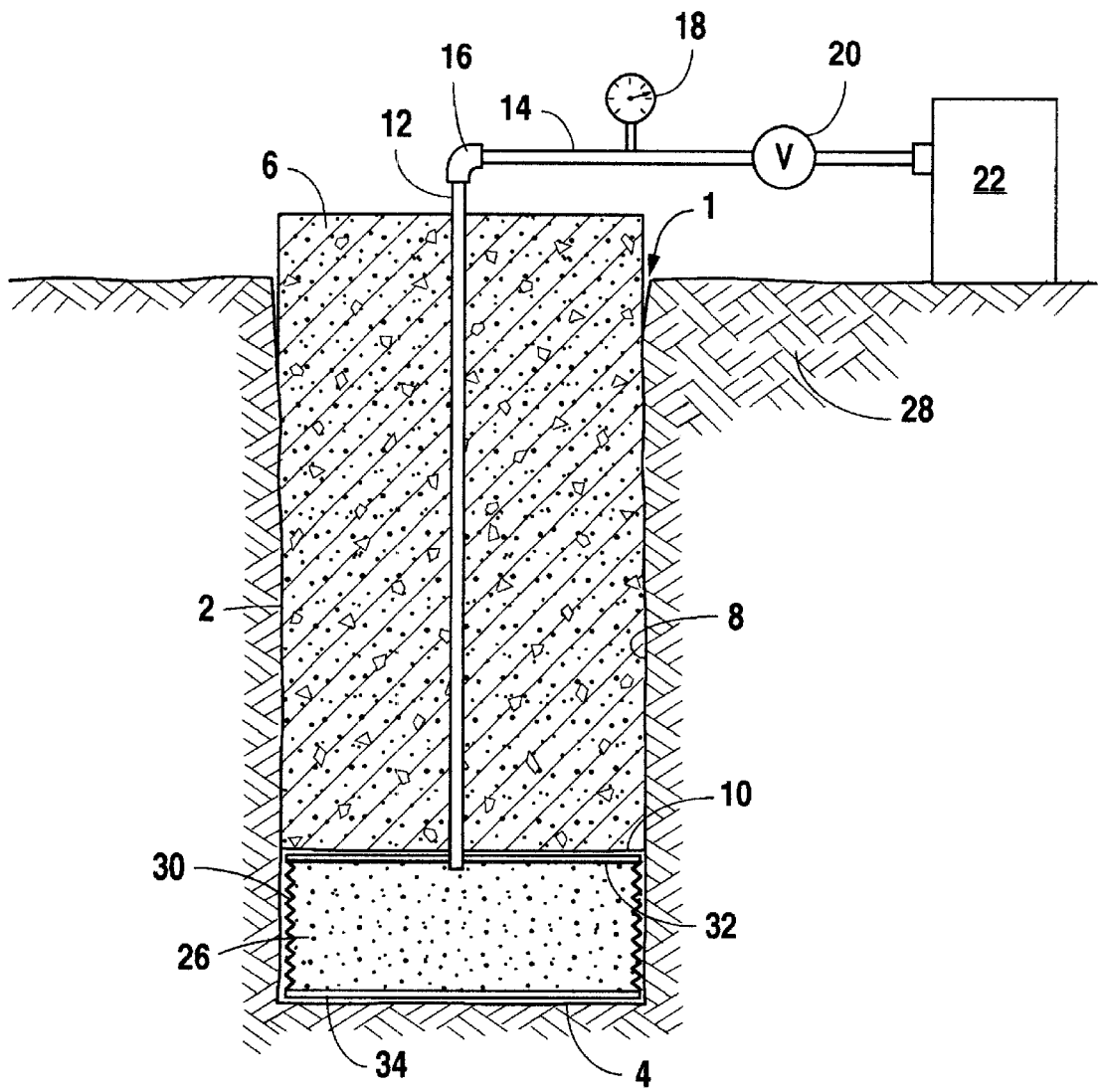
FIG. 2 is a cross-sectional view of an embodiment of the invention employing bellows apparatus to stress the pier.

Another embodiment is shown in FIG. 2, wherein the grout enclosure comprises bellows 30 including hard upper plate 32 and lower plate 34. Plates 32 and 34 are preferably steel disks, but may be made from any sufficiently hard material. Upper plate 32 is adapted to receive conduit 12. Bellows 30 ensure that the enclosure fills substantially all of the cavity under the pier by minimizing the risk of folding or gathering that may occur with a rubber bladder. Likewise, bellows 30 provide more uniform pressure application at the shaft floor 4 and the lower end 10 of pier 6.

Figure 3:
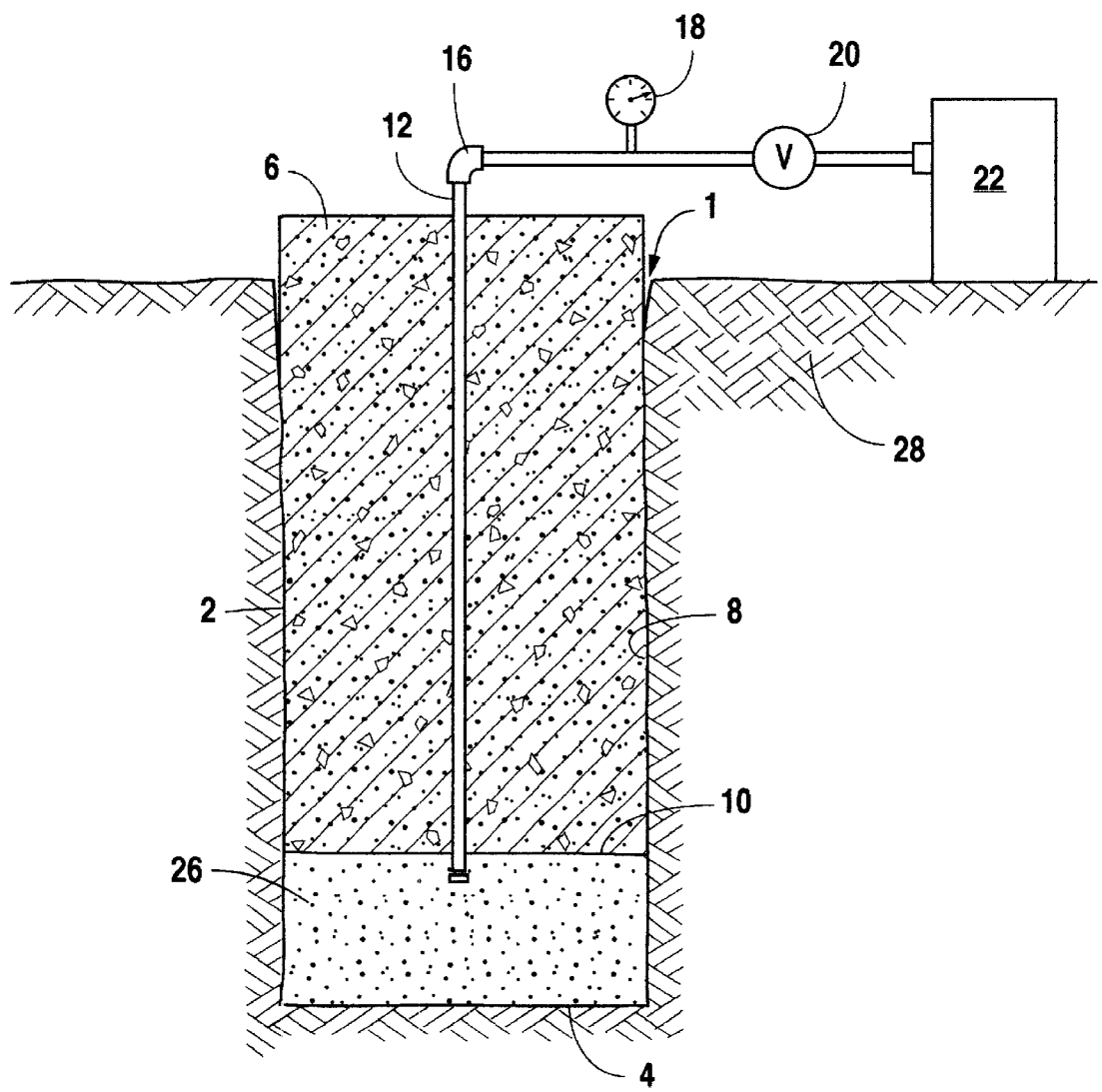
FIG. 3 is a cross-sectional view of another embodiment in which the shaft and concrete pier portion contain the pressurized grout of the invention.

FIG. 3 shows another embodiment of the post-base-stressed pier assembly in which the pressurized grout 26 is not contained by a structural enclosure such as a bladder or bellows. In suitable hard earthen material 28, such as rock, shaft wall 2 and shaft floor 4 may be used to contain the pressurized grout beneath lower end 10 of pier 6. In this embodiment, conduit 12 is lowered into shaft 1 without an attached enclosure. A cage or other suitable apparatus may be employed to position conduit 12 and hold it in place while concrete pier 6 is poured. Snug-fitting blow-out plug 36 ensures that fluid concrete poured for the pier will not enter the conduit 12 in advance of the pressurized grout and cause blockage. Plug 36 is ejected when pressurized grout is forced through conduit 12 after pier 6 hardens. The hardness of earthen material 28 prevents pressurized grout 26 from being forced substantially upward alongside pier wall 8. The post-base-stressed pier is thus formed by concrete pier 6 and hardened pressurized grout 26 contained by the shaft wall and floor. Pressurized grout 26 exerts an upward force against pier 6 at its lower end 10, in a manner similar to the enclosure of FIGS. 1 and 2.

Figure 4:
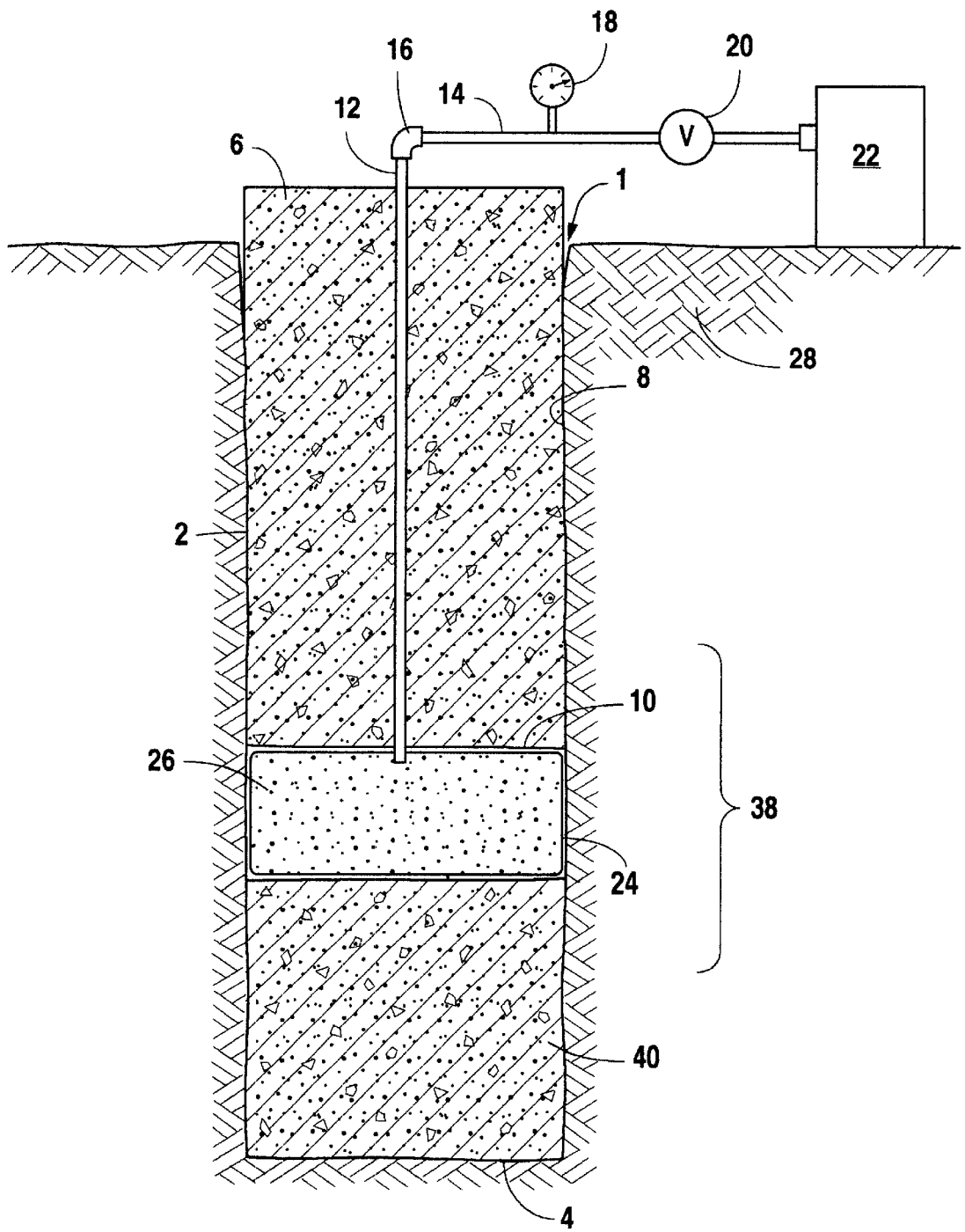
FIG. 4 is a cross-sectional view of another embodiment in which the pier is post-stressed by grout injected intermediate two pier portions along the length of a pier.

An alternative embodiment of a post-stressed pile according to the invention is shown in FIG. 4. In this embodiment, the pier 6 comprises a proximal portion of a pier together with a distal portion 40 within shaft 1. Distal pier portion 40 is formed in conventional fashion in shaft 1. Enclosure 24 is thereafter placed in shaft 1. Pier 6 is formed, resulting in a bisected pier 38. Enclosure 24 is filled with pressurized grout 26 according to the procedures for constructing a continuous post-base-stressed pier given with respect to FIG. 1 hereinabove. In lieu of enclosure 24, pressurized grout may be delivered to bellows 30 as in FIG. 2, or shaft wall 2 and distal pier portion 40 of the bisected pier may be used to contain the pressurized grout beneath lower end 10 of pier 6. A bisected pier configuration according to this embodiment may be selected when, for example, earthen material 28 near the shaft floor 4 is too soft to adequately contain enclosure 24 when filled with pressurized grout 26, and harder ground conditions prevail higher in shaft 1.

While particular embodiments of the invention have been illustrated and described, it will be obvious to those skilled in the art that various changes and modifications may be made without sacrificing the advantages provided by the principles of construction and operation disclosed herein.

What is claimed is:

1. A structural pier assembly with enhanced load bearing capacity for supporting foundations, bridges and other loads, comprising:
   a cementitious pier disposed in a shaft and characterized by a weight; and
   an enclosure positioned beneath said cementitious pier, said enclosure containing grout hardened under pressure exerted through a conduit, and said enclosure exerting an upward force on said cementitious pier, thereby enhancing the load bearing capacity of said structural pier assembly.

2. The structural pier assembly of claim 1, wherein said upward force exceeds the weight of the cementitious pier.

3. The structural pier assembly of claim 2, wherein said enclosure comprises a bladder.

4. The structural pier assembly of claim 3, wherein said bladder is rubber.

5. The structural pier assembly of claim 2, wherein said enclosure comprises bellows.

6. The structural pier assembly of claim 5, wherein said bellows comprise upper and lower metal plates.

7. The structural pier assembly of claim 1, wherein said conduit extends axially along the length of said cementitious pier for delivering said pressurized grout to said enclosure.

8. The structural pier assembly of claim 1, further comprising a distal pier portion, said enclosure disposed between said cementitious pier and said distal pier portion, thereby to form a bisected pier having enhanced load bearing capacity.

9. A structural pier assembly with enhanced load bearing capacity for supporting foundations, bridges and other loads, comprising:
   a cementitious pier disposed in a shaft and characterized by a weight; and
   grout placed beneath said cementitious pier through a conduit and hardened under pressure exerted through said conduit, and said grout exerting an upward force on said pier to enhance the load bearing capacity of said structural pier assembly.

10. The structural pier assembly of claim 9, wherein said upward force exceeds the weight of the cementitious pier.

11. The structural pier assembly of claim 10, wherein said conduit extends axially along the length of said cementitious pier for delivering said pressurized grout beneath said cementitious pier.

12. The structural pier assembly of claim 10, wherein said cementitious pier has a wall and said pressurized grout does not extend substantially upward alongside the pier wall.

13. The structural pier assembly of claim 9, further comprising a distal pier portion, said pressurized grout disposed between said cementitious pier and said distal pier portion, thereby to form a bisected pier having enhanced load bearing capacity.

14. A method of enhancing the load bearing capacity of a structural cementitious pier characterized by a weight, comprising the steps of:
   placing an enclosure in a shaft formed in earthen material, said enclosure being adapted to receive fluid grout through a conduit;
   forming a cementitious pier above said enclosure;
   placing pressurized grout in said enclosure through said conduit so as to exert an upward force against said cementitious pier; and
   allowing the grout to harden while remaining pressurized through said conduit.

15. The method of claim 14, wherein said upward force exceeds the weight of the cementitious pier.

16. The method of claim 15, wherein said enclosure comprises a bladder.

17. The method of claim 16, wherein said bladder is rubber.

18. The method of claim 15, wherein said enclosure comprises bellows.

19. The method of claim 18, wherein said bellows comprise upper and lower metal plates.

20. The method of claim 19, wherein said enclosure is coupled to a conduit and said cementitious pier is formed so that said conduit extends axially along the length of said cementitious pier.

21. The method of claim 14, further comprising forming a distal pier portion in said shaft before said enclosure is placed in the shaft.

22. A method of enhancing the load bearing capacity of a structural cementitious pier characterized by a weight, comprising the steps of:

forming a cementitious pier in a shaft formed in earthen material;

placing pressurized grout beneath said cementitious pier through a conduit so as to exert an upward force against said cementitious pier; and allowing the grout to harden while remaining pressurized through said conduit.

23. The method of claim 22, wherein said upward force exceeds the weight of the cementitious pier.

24. The method of claim 23, further comprising the step of extending said conduit axially along the length of said cementitious pier.

25. The method of claim 23, wherein said cementitious pier has a wall and said pressurized grout does not extend substantially upward alongside the pier wall.

26. The method of claim 22, further comprising forming a distal pier portion in said shaft before forming said cementitious pier, and placing said pressurized grout between said distal pier portion and said cementitious pier, thereby to form a bisected pier having enhanced load bearing capacity.

27. A method of determining the enhanced load bearing capacity of a structural cementitious pier, comprising the steps of:

placing an enclosure in a shaft formed in earthen material and having a floor, said enclosure being adapted to receive fluid grout through a conduit;

forming a cementitious pier above said enclosure;

placing pressurized grout in said enclosure through said conduit so as to exert an upward force against said cementitious pier and a downward force against the floor of the shaft, said upward force generating skin friction against said cementitious pier;

allowing the grout to harden while remaining pressurized through said conduit;

measuring the pressure of the grout to obtain said upward and downward forces; and using the measured pressure to calculate an end bearing capacity and a side bearing capacity for the cementitious pier.

28. The method of claim 27, wherein said load bearing capacity is a function of twice the end bearing capacity.

29. The method of claim 27, wherein said load bearing capacity is a function of twice the skin friction.

* * * * *